(12) United States Patent
Foucher et al.

(10) Patent No.: US 9,418,039 B2
(45) Date of Patent: Aug. 16, 2016

(54) DEVICE FOR MONITORING THE INTEGRITY AND SOUNDNESS OF A MECHANICAL STRUCTURE, AND METHOD FOR OPERATING SUCH A DEVICE

(75) Inventors: Bruno Foucher, Chatillon sous Bagneux (FR); Vincent Rouet, Orgeval (FR); Remy Reynet, Simiane Collongue (FR)

(73) Assignees: AIRBUS GROUP SAS, Blagnac (FR); EUROCOPTER, Marignane (FR)

( * ) Notice: Subject to any disclaimer, the term of this patent is extended or adjusted under 35 U.S.C. 154(b) by 98 days.

(21) Appl. No.: 13/982,426

(22) PCT Filed: Jan. 31, 2012

(86) PCT No.: PCT/FR2012/050201
§ 371 (c)(1),
(2), (4) Date: Jul. 29, 2013

(87) PCT Pub. No.: WO2012/104539
PCT Pub. Date: Aug. 9, 2012

(65) Prior Publication Data
US 2013/0307703 A1  Nov. 21, 2013

(30) Foreign Application Priority Data
Jan. 31, 2011 (FR) ...................................... 11 50700

(51) Int. Cl.
*G08B 21/00* (2006.01)
*G08G 1/123* (2006.01)
(Continued)

(52) U.S. Cl.
CPC ............. *G06F 15/0275* (2013.01); *G01M 5/00* (2013.01); *G01N 37/00* (2013.01); *G07C 5/008* (2013.01); *G07C 5/085* (2013.01)

(58) Field of Classification Search
CPC ............ G08C 19/02; G08C 19/14; F21S 8/02; B64D 45/0015; G08B 13/08; G01N 27/121; G01N 29/11; A63B 2220/40; G01L 7/00
USPC ............. 340/870.3, 693.2, 945, 686.1, 13.26; 73/29.02, 488, 584, 700
See application file for complete search history.

(56) References Cited

U.S. PATENT DOCUMENTS 5,926,110 A * 7/1999 Downs ............... G06K 19/0723
                                                340/10.51
8,635,916 B1 * 1/2014 Loverich ............... G01L 5/0004
                                                73/768

(Continued)

FOREIGN PATENT DOCUMENTS

WO      2008/059226 A2      5/2008

*Primary Examiner* — George Bugg
*Assistant Examiner* — Munear Akki
(74) *Attorney, Agent, or Firm* — Im IP Law PLLC; C. Andrew Im

(57) ABSTRACT

The invention relates to a device for monitoring the integrity and soundness of a mechanical structure, such as an aircraft. The device comprises a control unit, a radio frequency transmission means, and an electric battery. The control unit recovers data from a set of digital and/or analog sensors. The radio frequency transmission means enables the control unit to transmit the data received from the sensors to a man/machine interface. The electric battery powers the device and is rechargeable. The device further comprises a module for recovering electromagnetic energy capable of converting the recovered electromagnetic energy into electric power so as to recharge the battery and/or directly power the device.

11 Claims, 3 Drawing Sheets

(51) Int. Cl.
*G08C 19/38* (2006.01)
*G08C 19/12* (2006.01)
*G01N 19/10* (2006.01)
*G01P 15/00* (2006.01)
*G01N 29/00* (2006.01)
*G01L 7/00* (2006.01)
*G06F 15/02* (2006.01)
*G01M 5/00* (2006.01)
*G07C 5/00* (2006.01)
*G07C 5/08* (2006.01)
*G01N 37/00* (2006.01)

(56) References Cited

U.S. PATENT DOCUMENTS

| | | |
|---|---|---|
| 2007/0114422 A1 | 5/2007 | Berkcan et al. |
| 2008/0036617 A1* | 2/2008 | Arms .................. B64C 27/006 340/679 |
| 2008/0047363 A1 | 2/2008 | Arms et al. |
| 2010/0090866 A1* | 4/2010 | Chen ........................ B64G 6/00 340/953 |
| 2010/0308794 A1 | 12/2010 | Townsend et al. |
| 2011/0080135 A1* | 4/2011 | Bland .......................... 320/101 |

* cited by examiner

DEVICE FOR MONITORING THE INTEGRITY AND SOUNDNESS OF A MECHANICAL STRUCTURE, AND METHOD FOR OPERATING SUCH A DEVICE

RELATED APPLICATIONS

This application is a §371 application from PCT/FR2012/050201 filed Jan. 31, 2012, which claims priority from French Patent Application No. 11 50700 filed Jan. 31, 2011, each of which is herein incorporated by reference in its entirety.

TECHNICAL FIELD OF INVENTION

The present invention concerns a device for observing the entirety and the wholeness of a mechanical structure and a method of functioning for such a device. It applies itself in particular, to the observation of mechanical entirety and wholeness of different composite material elements or objects, constituting an aeronautic structure.

BACKGROUND OF THE INVENTION

As is the technique, the observation of the mechanical entirety and wholeness of different composite material elements and objects forming a structure of an aircraft, is currently carried out by means of inspections. The said inspections are carried out by one or several operators. These inspections are generally carried out before and/or after each flight of the aircraft. These inspections represent a percentage of considerable accumulated time, in the lifecycle of the aircraft.

There is therefore a need of automation of these processes of observation to allow a saving of time and money for each one of the airlines.

However, arriving at such an automation of these processes is not possible in the aeronautic area, without interference of the said observation devices with the control system of the aircraft, or of the autonomy and of the size of the observation device, together with the costs required to put in place or to replace these devices.

So, in the aeronautic area, the skilled person uses certain software applications which explore the conditions of the structure of the aircraft when it is on the ground and/or control the mechanical entirety and wholeness of the objects or elements of the said structure, when, for example, the said objects or the said elements have been repaired during maintenance or upkeep of the aircraft.

These software applications are suitable for collecting data received from a set of sensors. These sensors are divided over the whole structure of the aircraft and connected in networks, so as to be able to observe the critical parts of the composite materials during upkeep or following emergency conditions subjected by the aircraft during a phase of flight.

However, none of the existing solutions are truly universal, since the sensors and software used are different from one airline to another and/or from one country to another. It is therefore difficult to ensure effective monitoring in these conditions of a history of the subjected constraints, together with the mechanical entirety and wholeness of the different objects and/or elements of the aircraft. That, so as to anticipate possible damage and/or wear and tear of the said objects, could consequently lead to more or less serious accidents for these aircrafts.

OBJECT AND SUMMARY OF THE INVENTION

The present invention aims to remedy, in whole or part, the disadvantages of the techniques previously displayed.

For that, the invention proposes a device for observing the entirety and the wholeness of a mechanical structure, together with a method of functioning for such a device. The device, according to the invention, is suitable to be integrated with all types of object or element of the structure of the aircraft. This integration of the device, according to the invention is carried out either by bonding to the surface of the object or the element of the aircraft, or directly by insertion into the penultimate composite layer of the said object or of the said element. To do this, the said device has a shape, practically identical to that of a bank card, with a thickness of around a few millimeters, to ease its integration.

Despite its small size, the device, according to the invention, comprises wireless means, allowing it on the one hand, to send data to a human/machine interface or reader used by an operator, and on the other hand, to avoid the putting in place or the replacement of cabling for the sensors placed on the structure of the aircraft.

Additionally, the device, according to the invention, is not connected to a specific type of sensor. Indeed, the invention proposes a modular observation device, configured to offer a standardised interface, where all types of sensor can be connected in accordance with applications desired by the operator.

Also, the device, according to the invention, comprises a calculator or control unit equipped with a sufficient processing power, to process all necessary data for the observation of the object or of the element of the aircraft. This, so that the operator can carry out analyses via the human/machine interface put in the proximity of the device according to the invention, associated with an object or an element of the aircraft, and in accordance with different dynamically configurable parameters. So, the invention no longer requires, as is the technique, a support to make the software applications function, in order to collect and process the data from the sensors.

The device, according to the invention, also comprises means suitable for interfacing itself automatically with one or several energy salvage systems. These energy salvage systems are suitable for electrically supplying the device, according to the invention. The device, according to the invention, comprises means suitable for effectively operating and managing the electric energy received and/or accumulated. The device, according to the invention, is therefore suitable for ensuring its own autonomy of functioning during the whole lifecycle of the aircraft.

BRIEF DESCRIPTION OF THE DRAWINGS

The invention will be included in the reading of the following description, and in the examination of the figures which supports it. These are presented for information purposes only, and in no way limiting of the invention.

DETAILED DESCRIPTION OF THE EMBODIMENTS

Figure 1:
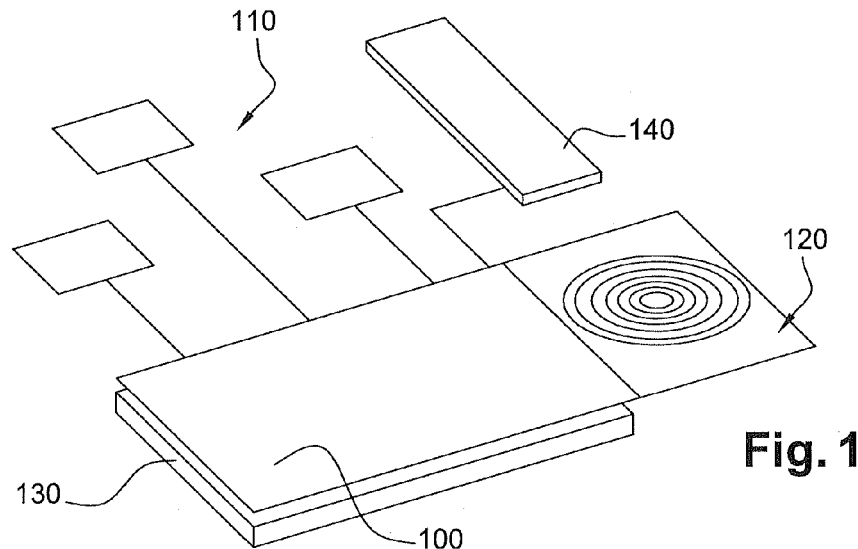
FIG. 1 illustrates a diagrammatic representation of the device, according to a way of carrying out the invention.

FIG. 1 shows a control unit 100 connected to a set of sensors 110 and a means 120 of wireless transmission/reception. The control unit 100, the means 120 of transmission/reception and the set of sensors 110, are supplied in electrical energy by an accumulator 130, suitable to be recharged. In a preferred way of fulfillment, the accumulator 130 is a Li-ion type battery. This accumulator 130 is suitable to be electrically recharged by a means 120 of integrated electromagnetic connection, or by an outside unit 140 of energy salvage, in order to convert into electrical energy. This unit 140 of energy salvage is a nanoscale electrical generator. Indeed, this generator 140 is suitable for converting mechanical type energy into electrical energy, such as vibrations, a dispersal of fluid, a biological movement, or solar type energy, or electromagnetic type energy, or yet calorific type energy.

Figure 4:
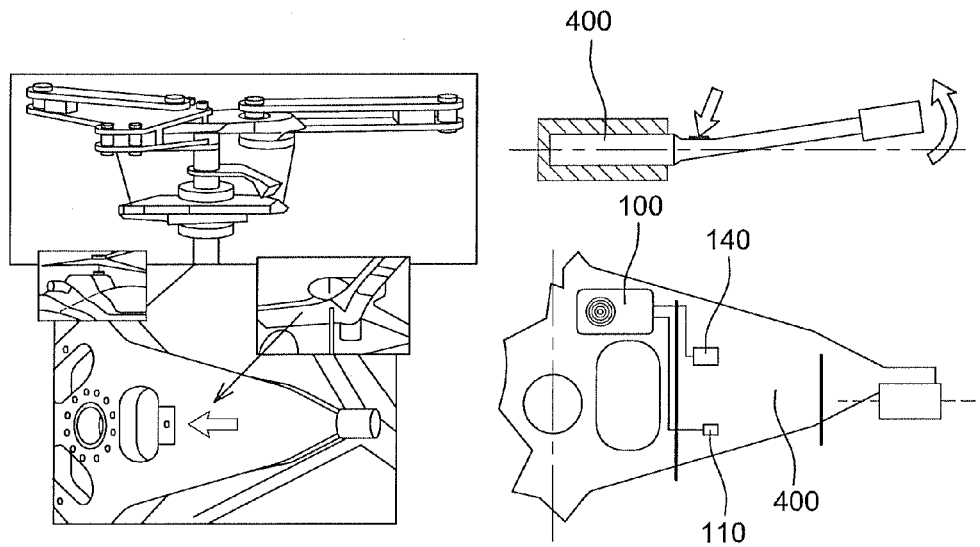
FIG. 4 shows an example of using the device, according to way of carrying out the invention.

The control unit 100, the means 120 of transmission/reception, and the accumulator 130 are suitable for being put in a case, of which the dimensions are equivalent to those of a credit card. In a way of fulfillment, the case has a length of 85 mm, a width of 55 mm, and a thickness of a few millimeters. These dimensions allow, in a preferred way of fulfillment, an integration of the device, according to the invention, in the penultimate composite material layer of an object 400 or of an element, making up the structure of an aircraft as shown in FIG. 4. Alternatively, the device is suitable for bonding itself to the surface of the said object or of the said element.

Figure 2:
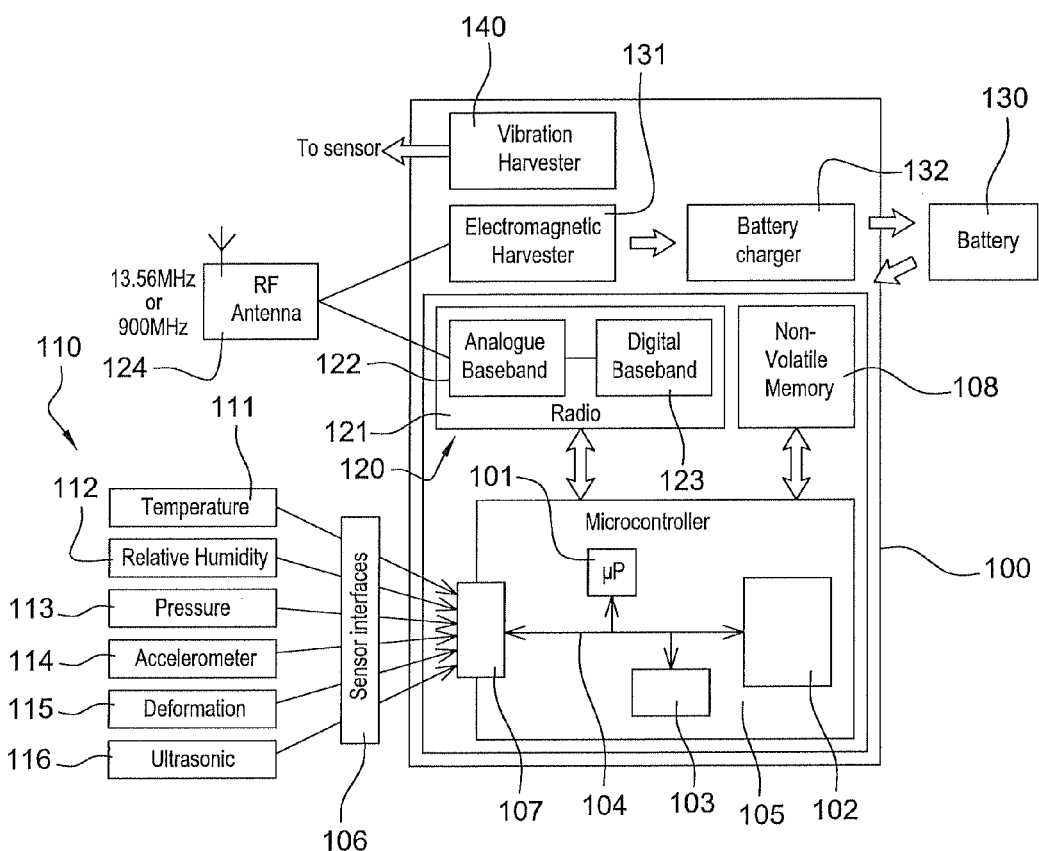
FIG. 2 shows a structure of different elements making up the device, according to a way of carrying out the invention.

FIG. 2 shows a detailed view of the different elements making up the device, according to the invention. Indeed, the control unit 100 comprises a microprocessor 101, a program memory 102 and a data memory 103 interlinked with each other via a set of communication buses 104. In a way of carrying out the invention, the microprocessor 101, the program memory 102, the data memory 103 and the communication buses are integrated in a microcontroller 105. The control unit 100 comprises an input/output interface 106, having a digital analogue converter 107, allowing the connection and the transfer of data between the microcontroller 105 and the set of sensors 110 via a set of communication buses. The set of sensors 110 comprises, in a non-exhaustive way, a temperature sensor 111, a humidity sensor 112, a pressure sensor 113, an accelerometer 114, a distortion sensor 115, and an ultrasound sensor 116. These sensors 110 have as a characteristic, the fact that each does not consume a lot of electrical energy.

The control unit 100 is connected in a bidirectional way, with the means of transmission/reception 120. These means of transmission/reception 120 comprise a set of material layers, which are respectively, a radio layer 121, an analogue band base layer 122, a digital band base layer 123, a data-link controller (not shown) and a data-link administrator (not shown). The radio layer 121 is connected to a radio frequency antenna 124, so as to emit and receive data. In a way of carrying out the invention, the frequencies used to emit or receive data from the antenna are either 13.56 MHz or 900 MHz.

The control unit 100 also comprises a non-volatile data memory 108, with which it communicates in a bidirectional way.

The control unit 100 is, as previously indicated, supplied by the battery 130. However, as this control unit 100 is intended to end up irreversibly bonded to the surface or integrated in the penultimate composite material layer of an object or of an element of the aircraft, the invention is intended to recharge the battery 130, the putting into place in the control unit 100 of an electromagnetic energy salvage unit 131. So, during the reception or the emission of data by means of the antenna 124, surrounding electromagnetic waves are absorbed to be converted into electrical energy. This salvaged electrical energy from the electromagnetic waves is then stored up by the battery 130 via a charge control unit 132. Consequently, this unit 132 will be named charger.

To not quickly discharge the battery 130, the invention intends for the presence of a mechanical energy salvage unit 140, more particularly allowing the conversion of vibratory or seismic energy, in order to transform into electrical energy. This unit 140 is intended to supply the set of sensors 110, connected to the control unit 100. The interest of the putting in place of a vibratory energy salvage unit 140 is to be able to supply the sensor linked to the vibrations and the heat sensor, when the aircraft is functioning. In the description, it is understood by the fact that the aircraft is functioning, the fact that at least one of the aircraft's motors is working. So, when at least one of the aircraft's motors is working, the structure of the aircraft is subjected to more or less significant vibrations, but sufficient to supply the unit 140.

Figure 3:
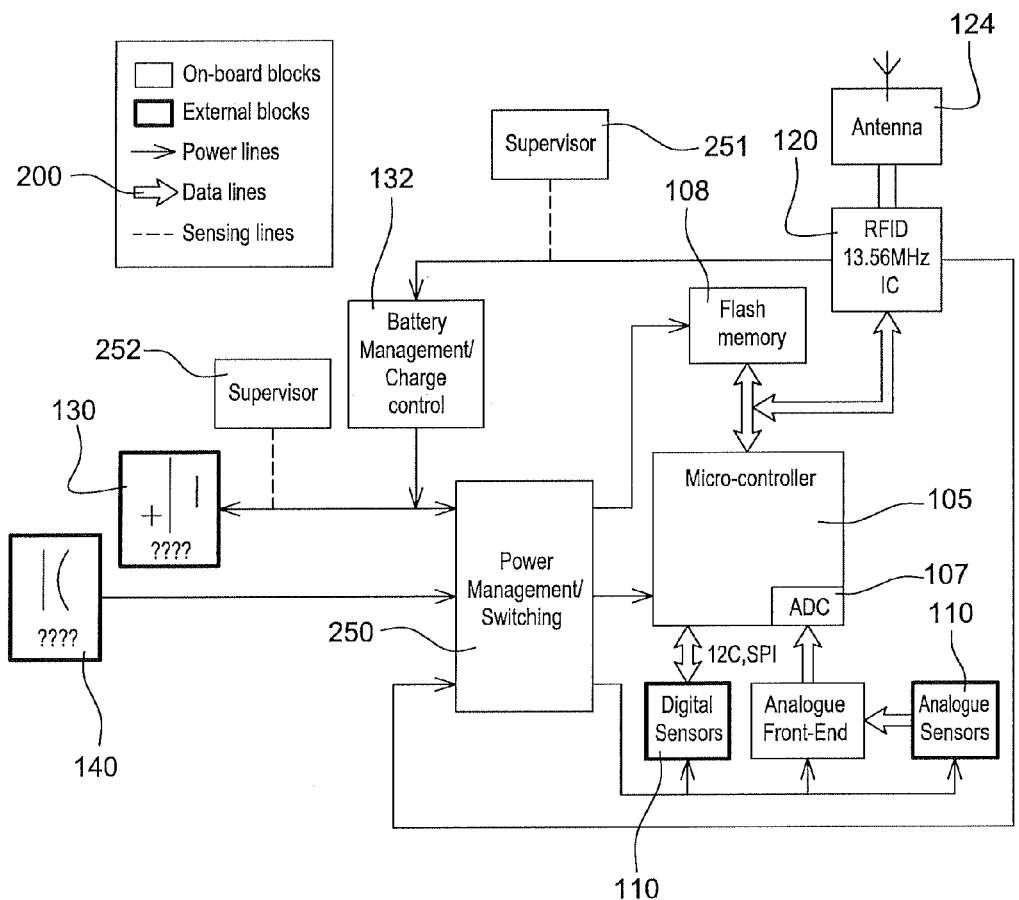
FIG. 3 is a functional diagram of the device, according to a way of carrying out the invention.

FIG. 3 is a diagrammatic representation of the different interactions between each functional unit of the device, according to a way of carrying out the invention. On this FIG. 3, it is observed that the microcontroller 105 is suitable for communicating according to a master-slave diagram, via an SPI (Serial Peripheral Interface) link 200, with different digital and analogue sensors 110, the data memory 108 and the means of transmission 120. In the way of fulfillment of FIG. 3, the means of transmission is an RFID (Radio Frequency, Identification) chip.

Alternatively, the different digital sensors communicate with the control unit 100 by means of an I$^2$C (Inter Integrated Circuit) bus.

Actions led by the microcontroller 105, are ordered by the microprocessor 101. The microprocessor 101 produces, in response to the instruction codes recorded in the program memory 102, orders intended for different systems of the control unit 100 of the device, according to the invention.

The management of supplying the control unit 100 and these systems 110, 108 is attributed to a unit 250. This unit 250 is suitable for receiving electrical energy which either comes from the battery 130, and/or comes from the supercapacitor, previously supplied by the vibratory energy salvage unit 140, and/or coming directly from the electromagnetic energy salvage unit 131. The unit 250 is suitable for electrically supplying the microcontroller 105, the data memory 108 and the sensors 110. The means 120 of transmission/reception is a passive element, not requiring any energy source outside of the one supplied by a human/machine interface (not shown) at the time of the collection of data. At the time of the data collection by the operator, the surrounding electromagnetic waves are converted into electrical energy by the unit 131, and then directed towards the charger 132 of the battery 130. Two units 251, 252 of control of the current are placed respectively before the charger 132, and after the battery 130, so that the unit 250 of management of supply, determines the current coming from the electromagnetic energy salvage unit 131, but also the current supplied or stored up by the battery 130.

The invention is not limited to only vibratory and electromagnetic energy salvagers. Indeed, other types of energy salvager can be connected to the device of the invention, in accordance with the area of application, in order to ensure an observation of the structure of the aircraft.

Figure 5:
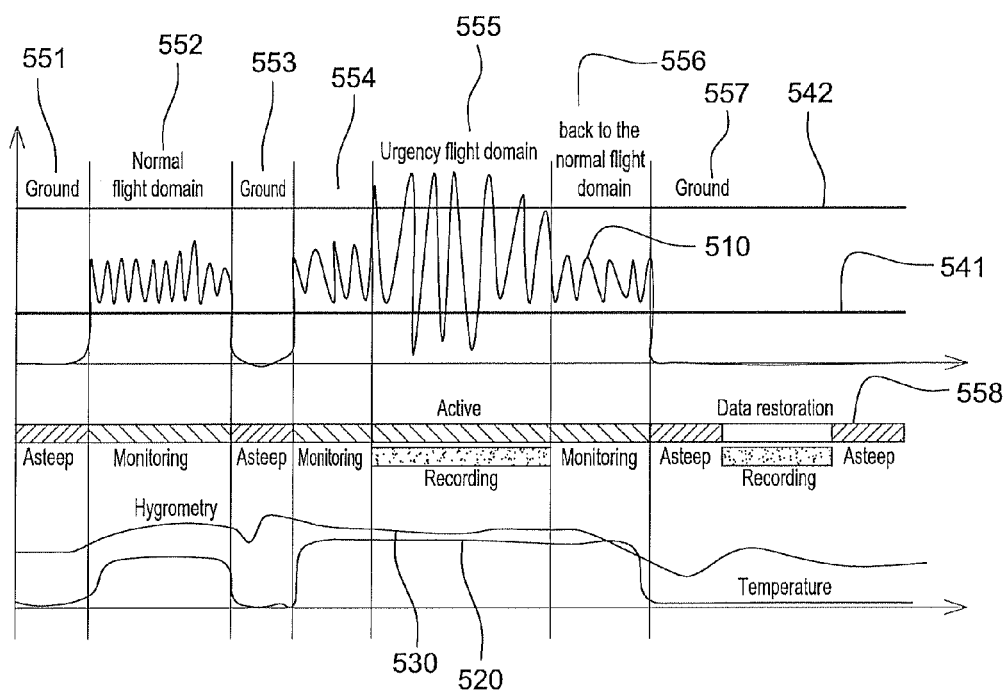
FIG. 5 shows an example of curves established from the data collected for different sensors associated with the device, according to a way of carrying out the invention.

FIG. 5 shows an example of curves established from the data collected for different sensors associated with the device, according to a way of carrying out the invention.

In FIG. 5, three curves 510, 520, 530 can be seen, of which a first curve 510 relates to the distortion sensor 115, a second curve 520 relates to the temperature sensor 111, and a third curve 530 relates to the hygrometry sensor 112. These curves

510, 520, 530 allow to see what the data is that will be recorded in accordance with the different phases of flight of the aircraft. The control unit 100 considers three phases of flight of the aircraft. A first phase 551, 553, 557 of flight of the aircraft corresponds to the fact that the aircraft is on the ground. A second phase 552, 554, 556 of the aircraft corresponds to the fact that the aircraft is carrying out a flight known as normal. In the invention, it is considered that the aircraft carries out a normal flight, when the signal received by the control unit 100 from the sensor 111, 112, 113, 114, 115, 116, is included between a previously determined limit 541 of observation and a previously determined limit 542 of recording. A third phase 555 corresponds to the fact that the aircraft is subjected to an emergency situation during its flight, when the signal, received by the control unit 100 from the sensor 111, 112, 113, 114, 115, 116, is higher than or equal to the limit of recording 542, plus a few seconds preceding or succeeding this time.

So, it is understood from the curve 510, that during a step 551, the aircraft is on the ground, the sensor 115 is on standby.

At a step 552, the aircraft is in a phase of flight, considered here as normal. The sensor 115 measures data all along this phase of flight, and the control unit 100 checks that this data is included purely between the limit 541 of observation and the limit 542 of recording. As there is nothing to signal, the control unit 100 does not record data.

At a step 553, the aircraft is once again on the ground, the sensor 115 is on standby.

At a step 554, the aircraft is in a phase of flight, considered as normal. The sensor 115 measures data all along this phase of flight, the control unit 100 checks that this data is included purely between the limit 541 of observation and the limit 542 of recording. As there is nothing to signal, the control unit 100 does not record data.

At a step 555, the aircraft is subjected to a significant stress during its flight. The sensor 115 measures data all along this phase of flight, the control unit 100 checks that this data is included purely between the limit 541 of observation and the limit 542 of recording. As the signal received by the control unit 100 is higher than the limit of recording 542, then the control unit 100 proceeds to record data. During this same phase of flight, data relating to the curve 520 of temperature and the curve 530 of hygrometry is also recorded. During a short period of a few seconds preceding and succeeding the significant stress, data from different sensors will also be recorded. These recordings will allow the operator to determine the source(s) of the problem which has led to this emergency situation during the flight.

At a step 556, the aircraft is in a phase of flight, considered as normal. The sensor 115 measures data all along this phase of flight, the control unit 100 checks that this data is included purely between the limit 541 of observation and the limit 542 of recording. As there is nothing to signal, the control unit 100 does not record data.

At a step 557, the aircraft is once again on the ground, and the sensor is on standby.

At a step 558, the aircraft is in a phase of maintenance or upkeep, and an operator, having its human/machine interface (not shown), comes to salvage the data recorded by the device of the invention. During this phase, the battery 130 of the device of the invention is recharged via electromagnetic waves emitted by the human/machine interface or the reader.

The invention claimed is:

1. A device for monitoring integrity and soundness of a mechanical structure of an aircraft, comprising:
   a control unit to collect data from a set of digital or analog sensors to monitor integrity and soundness of the mechanical structure of the aircraft, the sensors are active during a flight of the aircraft and on standby for the aircraft on the ground;
   a radio frequency transmitter for the control unit to transmit data received from the sensors to a human/machine interface;
   a rechargeable accumulator to supply electrical energy to the device; and
   an electromagnetic energy salvage unit to transform surrounding electromagnetic waves of the aircraft in flight into electrical energy to recharge the accumulator or directly supply the electrical energy to the device in response to a determination that the sensors are active, the electromagnetic energy salvage unit is on standby in response to a determination that the sensors are on standby.

2. The device of claim 1, further comprising an outside energy salvage unit configured to supply electrical energy to the device to ensure its energizing autonomy.

3. The device of claim 2, wherein the outside energy salvage unit is configured to convert into electrical energy from at least one of the following: mechanical energy, solar energy or calorific energy.

4. The device of claim 1, wherein the radio frequency transmitter is an RFID chip.

5. The device of claim 1, wherein the set of sensors comprises at least one of the following: a temperature sensor, a humidity sensor, a pressure sensor, an accelerometer, a distortion sensor, or an ultrasound sensor.

6. The device of claim 1, wherein the control unit, the radio frequency transmitter and the accumulator are configured to be housed in a case having dimensions equal to a credit card.

7. The device of claim 6, wherein the case has a length of 85 mm and a width of 55 mm.

8. The device of claim 6, wherein the case is integrated in a penultimate composite material layer of an object of the structure of the aircraft.

9. The device of 6, wherein the case is bonded to a surface of an object of the structure of the aircraft.

10. A method of operating a device of claim 1 for monitoring and soundness of the mechanical structure, comprising the steps of:
    salvaging outside energy to supply the device with the electrical energy;
    detecting signals from the set of sensors during a flight of the aircraft; and
    recording signal data during a period where at least one of the signals is higher than a predetermined limit, the signal data recording preceding and succeeding the period by one to two seconds.

11. The method of claim 10, further comprising the step of salvaging outside mechanical energy to supply the device with the electrical energy.

* * * * *